United States Patent
Tjäder et al.

(10) Patent No.: US 9,949,869 B2
(45) Date of Patent: Apr. 24, 2018

(54) INTRAUTERINE SYSTEM

(75) Inventors: Taina Tjäder, Littoinen (FI); Ulla Calvo Alonso, Piispanristi (FI); Pirjo Inki, Kaarina (FI); Harri Jukarainen, Kuusisto (FI); Ilkka Jutila, Littoinen (FI); Pirjo Kortesuo, Parainen (FI); Juha Lehtinen, Turku (FI); Eeva Lukkari-Lax, Espoo (FI); Heikki Lyytikäinen, Naantali (FI); Joachim Moede, Turku (FI); Hannu Nikander, Paattinen (FI); Pirjo Sallinen, Berlin (DE); Faisal Shafiq, Krefeld (DE); Wolfgang Kaufhold, Köln (DE); Christian Wamprecht, Neuss (DE)

(73) Assignee: BAYER OY, Turku (FI)

( * ) Notice: Subject to any disclaimer, the term of this patent is extended or adjusted under 35 U.S.C. 154(b) by 1196 days.

(21) Appl. No.: 13/499,701

(22) PCT Filed: Sep. 30, 2010

(86) PCT No.: PCT/FI2010/050753
§ 371 (c)(1),
(2), (4) Date: Jul. 20, 2012

(87) PCT Pub. No.: WO2011/039418
PCT Pub. Date: Apr. 7, 2011

(65) Prior Publication Data
US 2012/0272969 A1    Nov. 1, 2012

(30) Foreign Application Priority Data
Oct. 1, 2009  (FI) .................................... 20096003

(51) Int. Cl.
*A61F 6/14*  (2006.01)
*A61K 9/00*  (2006.01)

(52) U.S. Cl.
CPC ............ *A61F 6/142* (2013.01); *A61K 9/0039* (2013.01)

(58) Field of Classification Search
CPC ..... A61K 9/0036; A61K 9/0039; C08L 75/08; A61F 6/20; A61F 6/225; A61F 6/22;
(Continued)

(56) References Cited

U.S. PATENT DOCUMENTS 3,431,906 A * 3/1969 Taylor ........................... 128/839
3,892,238 A * 7/1975 Banford et al. .............. 128/839
(Continued)

FOREIGN PATENT DOCUMENTS

EP    0873751    10/1998
EP    1245639    10/2002
(Continued)

OTHER PUBLICATIONS

International Bureau of WIPO, International Preliminary Report on Patentability for International Patent Application No. PCT/FI2010/050753, dated Apr. 3, 2012, 5 pages.
(Continued)

*Primary Examiner* — Ophelia A Hawthorne
*Assistant Examiner* — Camtu Nguyen
(74) *Attorney, Agent, or Firm* — Nixon & Vanderhye P.C.

(57) ABSTRACT

The present invention relates to novel intrauterine systems and to methods for manufacturing these systems. An intrauterine system according to the invention comprises a reservoir and a continuous, closed and flexible frame. The frame comprises a thermoplastic polyurethane elastomer made of a polycarbonate diol, 1,6-hexamethylenediisocyanate, and a chain extender.

11 Claims, 6 Drawing Sheets

(58) Field of Classification Search
CPC .. A61F 6/202; A61F 6/14; A61F 6/142; A61F 6/146; A61B 17/12022
USPC ..... 525/438, 440.11; 424/432; 128/831, 833
See application file for complete search history.

(56) References Cited

U.S. PATENT DOCUMENTS

| | | | |
|---|---|---|---|
| 3,938,515 A * | 2/1976 | Leeper et al. | 424/432 |
| 4,156,067 A | 5/1979 | Gould | |
| 4,200,091 A | 4/1980 | Del Conte | |
| 4,789,720 A | 12/1988 | Teffenhart | |
| 5,993,972 A | 11/1999 | Reich et al. | |
| 6,527,995 B1 * | 3/2003 | Kaufhold | C08G 18/0895 264/126 |
| 2002/0082635 A1 | 6/2002 | Kammerer et al. | |
| 2003/0013792 A1 | 1/2003 | Muhlfeld et al. | |
| 2007/0265413 A1 * | 11/2007 | Peerlings | C08G 18/3221 528/79 |
| 2008/0095825 A1 | 4/2008 | Lafont | |
| 2009/0035350 A1 | 2/2009 | Stankus et al. | |
| 2009/0060973 A1 * | 3/2009 | Hunter | A61L 27/54 424/423 |
| 2011/0056501 A1 * | 3/2011 | Kortesuo | A61F 6/142 128/833 |

FOREIGN PATENT DOCUMENTS

| | | |
|---|---|---|
| EP | 1336631 | 8/2003 |
| EP | 1541100 | 6/2005 |
| EP | 1854818 | 11/2007 |
| FI | 97947 | 12/1996 |
| GB | 1318554 | 5/1973 |
| NL | 8601570 | 1/1988 |
| WO | WO 96/29026 * | 9/1996 |
| WO | 2000/051660 | 9/2000 |
| WO | 2008/007046 | 1/2008 |
| WO | 2009/122016 | 10/2009 |
| WO | WO 2009/122016 A1 | 10/2009 |

OTHER PUBLICATIONS

Swedish Patent Office, International Search Report and Written Opinion for International Patent Application No. PCT/FI2010/050753, dated Jan. 3, 2011, 9 pages.

Hasson, "Uterine geometry and IUCD design," BJOG: An International Journal of Obstetrics & Gynaecology, 89 (s4), 1982, pp. 1-10.

Kurz, "In vivo measurements of uterine cavities in 795 women of fertile age," Contraception. 29(6), Jun. 1984, pp. 495-510.

Randic, "Comparative Evaluation of Medicated and Non-medicated IUDs of the Same Size and Shape," Contracept Deliv Syst. 1(2), 1980, pp. 87-94.

USPTO, Non-final Office Action for U.S. Appl. No. 12/935,953, dated Aug. 16, 2012, 8 pages.

* cited by examiner

*a*            *b*

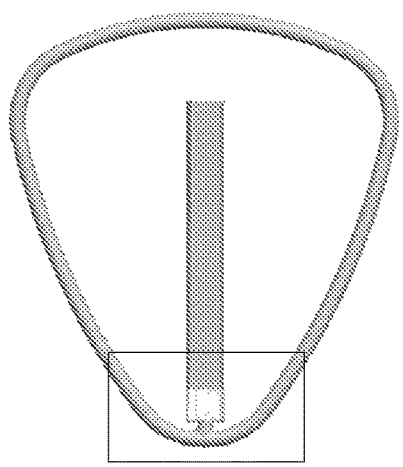
Figure 9
 
 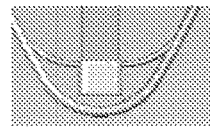

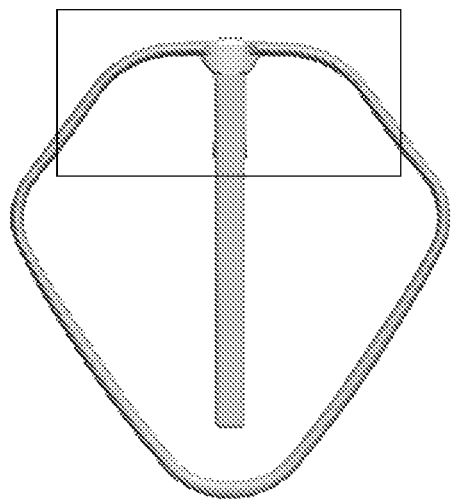
*Figure 10*
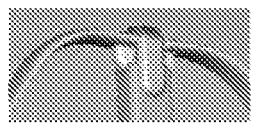 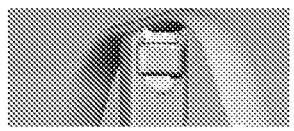
 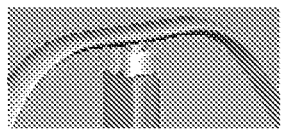

INTRAUTERINE SYSTEM

FIELD OF THE INVENTION

The present invention relates to novel intrauterine systems comprising a flexible, elastic frame comprising a thermoplastic polyurethane elastomer and a reservoir connected to the frame, wherein at least one end of the reservoir is connected to the inner surface of the frame and the reservoir comprises at least one therapeutically active substance. The invention is further related to a method for manufacturing these systems, and to a method for delivering therapeutically active substances to female mammals.

BACKGROUND OF THE INVENTION

A large number of different intrauterine devices have been proposed and applied in practice. The first IUDs that became generally used were large and extended the uterus and caused bleeding and pain, often accompanied by infections. There have been several attempts to overcome the disadvantages related to the intrauterine systems, and devices have been designed with modifications aiming to decrease pain and bleeding, to make insertion and removal easier, to limit the risk of expulsion and especially to minimize the risk of perforation.

Applicant's patent application FI 20085277 relates to an intrauterine delivery system comprising a frame and a reservoir connected to the frame, wherein the frame forms a continuous, closed and flexible system of polygonal, preferably triangular or pentagonal, shape and wherein at least one end of the reservoir is connected to the inner surface of the frame and the reservoir comprises at least one therapeutically active substance.

EP 0873751 by Takeda Chemical Industries discloses a biodegradable IUD wherein an active agent is dispersed in a biodegradable polymer which is mould to a predetermined shape of a ring. Said IUD does not comprise separate frame and reservoir structures. As such systems are usually hard and inflexible, introduction of rings made of such material to the human body is very difficult. If the ring-like structure of the device is broken during the degradation process, it would be extremely difficult to remove the device because it would be deformed and its hard, broken parts would cause tissue damage.

NL 8601570 by Futura Nova relates to an intrauterine device comprising an elongated stem which is combined to a ring of polymeric material. A contraceptive effect is achieved by covering the stem with a contraceptive material, preferably with metal and especially with copper in the form of a ring spiral on the stem. Said device does not comprise a separate reservoir consisting of a polymer matrix or polymer layer capable of controlling the release of the contraceptive material. Therefore the release rate of said contraceptive material could not be controlled but would depend on the solubility characteristics of the contraceptive.

GB 1,318,554 by Michael Reese Hospital & Medical Center describes an intrauterine device comprising at least one capsule containing a progestin contained within a partially permeable wall but not dispersed in any polymer matrix. In one embodiment the device comprises three silicone elastomer tubes containing progestin and joined by polyethylene corner pieces to form a generally ring shaped or triangular device. The device is said to have sufficient rigidity to maintain its shape when not subjected to outside forces, but still be easily flexed as required for insertion. However, although the ends of the silicone tubes need not to be sharp, it is likely that they irritate uterine wall thus impairing wearing comfort.

Many of the devices presented in the literature are bulky and/or rigid and may therefore cause side-effects and a high discontinuation rate. Undesirable complications that have been associated with the use of these intrauterine devices are pain and difficulties in insertion and/or in removal of the device, abdominal pain, infection, irregular bleeding, hormonal side effects, uterine perforation, cervical laceration, septic abortion, ectopic pregnancy, and expulsion of the IUS.

The optimal performance of an intrauterine system has been found to be determined largely by the interaction of the geometric parameters of the uterus and the device. The uterine cavity possesses a single axial and variable transverse and anteroposterior dimensions. Cyclic changes in uterine shape and size occur normally in women during different phases of the menstrual cycle. An ideal intrauterine system should be able to functionally adapt to the cyclic variations of the uterine cavity. Larger size of an IUD has been stated to increase the risk of expulsion and side effects. Abnormalities in uterine geometry as a result of congenital or acquired space-occupying lesions reduce the uterine space available for IUDs and increase further the probability of IUD expulsion and other clinical complications. The devices that are designed to fit to the size of the endometrial cavity are expected to have better performance records than those inserted at random, causing less irritation and less side effects (Kurz, Contraception. 1984 Jun. 29(6):495-510) and producing less endometrial trauma and consequently less bleeding (Randic, Contracept Deliv Syst. 1980; 1(2):87-94). The shape of the IUD should have blunt surfaces and gentle curves, and be devoid of sharp features which may cause uterine injury. Axial stiffness and transverse flexibility of the device appear to improve compliance properties (Hasson, BJOG, 89 (s4), 1-10, 1982).

In addition to dimensions and design characteristics material properties are important for an ideal intrauterine system.

With the devices where during the insertion procedure at least part of the device is outside the inserter tube, insertion pain is related to the outer diameter, design and flexibility of the insertion tube, but also to the size, design and flexibility of the device, especially of the part of the device laying outside the insertion tube. Pain soon after insertion usually occurs in the form of uterine cramps, and is probably related to uterine distention or irritation of the isthmic region caused by the device. The pain or discomfort is rarely present for more than the first weeks after the insertion.

It is also well known that the uterus contracts with a certain frequency continually and the contractions can push the device downward causing partial or complete expulsion. The contraction of the uterus will bring pressure on the inserted device. The transverse composition of forces will deform the device, and the longitudinal composition of forces will expel the device.

Therefore the material should be flexible but have a relatively high degree of stiffness (measured according to DIN 53504), preferably >8 $N/mm^2$ (at 100% elongation), especially more than 10 $N/mm^2$ (at 100% elongation). The material should also have a relatively high hardness (measured according to DIN 5305), preferably Shore D>38 and <60, more preferably Shore D>40 and <55). Moreover the material should have a high rebound (measured according to DIN 53512), preferably >30%, especially more than 35%. The cross section thickness must be sufficiently high to provide wanted resilience in use, and this depends on the material used. However, the stiffness and the thickness must not be so high as to prevent the device, the core, the frame or both from being bent through a substantial angle in use. Furthermore, it is important that the materials have a relatively high elasticity and characteristics which permit the device to be deformed and then again to return to its original configuration upon release of the deforming force.

Correct insertion, with the IUD placed up to the fundus, is thought to reduce the chances of expulsion and proper position of the device is necessary to achieve the optimal contraceptive efficacy.

Despite of the development work done, many intrauterine systems still have drawbacks. To overcome the issues related to various side effects described above and to improve patient compliance, intrauterine systems comprising a new material with excellent performance have been introduced. The intrauterine systems according to present invention can be easily inserted in the stable optimal position in the uterus and are comfortable to use. They are flexible and have a smooth shape to minimize the risk of perforation, but still with low possibility for expulsions, and do not have any pain causing elements or structural features.

BRIEF DESCRIPTION OF THE FIGURES

The invention is further illustrated by the following examples, describing various constructions of the intrauterine system according to the invention.

FIG. 3b illustrates the frame.

FIGS. 9 and 10 illustrate further examples of different methods to connect the reservoirs to the frame by using a metal or polymer insert, sleeve, supporting means, plug, staple, special clips, connectors, adapters, clothespin-type means or clamps or like.

OBJECT OF THE INVENTION

Figure 1:
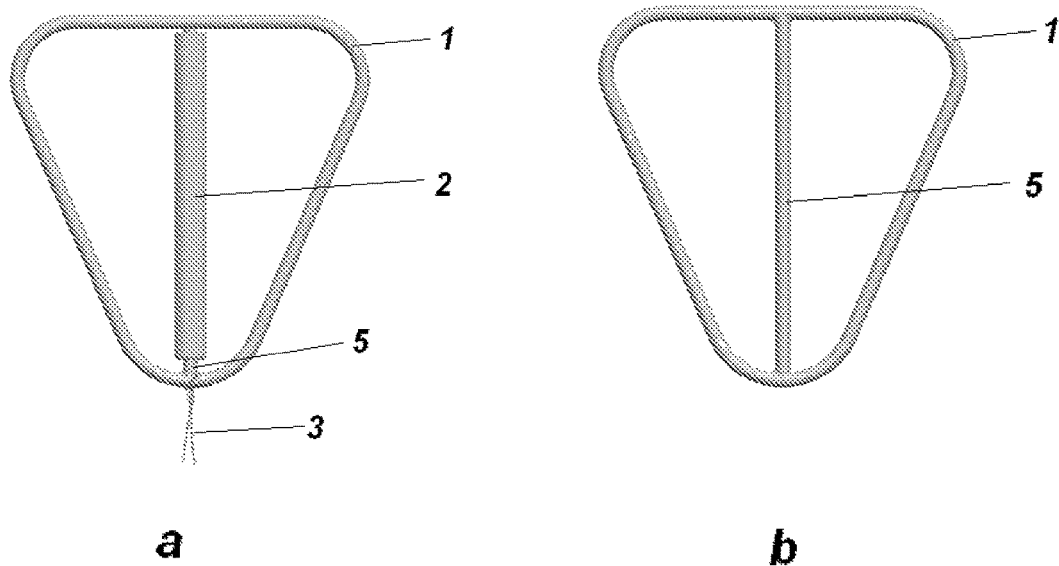
FIG. 1 illustrates an intrauterine system (FIG. 1a) and the corresponding frame (FIG. 1b). The frame has a triangular shaped frame (1) with rounded corners. The reservoir (2) is assembled on the shaft (5) connected both to the lower and to the upper part of the frame.
Figure 2:
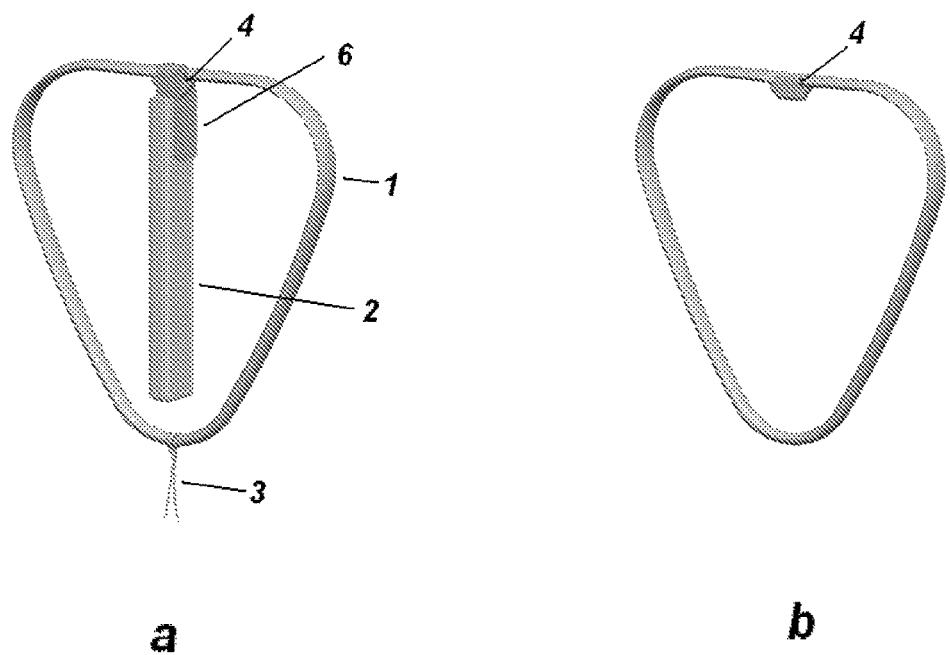
FIG. 2 illustrates an intrauterine system (FIG. 2a) and the corresponding frame (FIG. 2b). The frame (1) is a triangle with rounded corners and with flat cross section. The flat rectangular reservoir (2) is connected to the upper part of the frame by using a metal or polymer clip (6) and an extension (4) of the frame.
Figure 3:
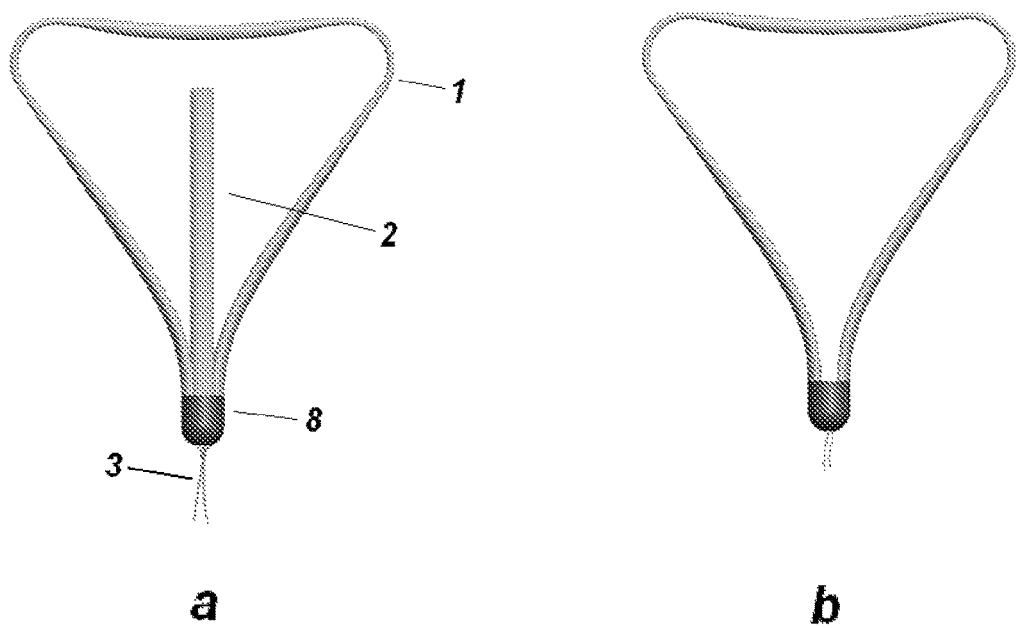
FIG. 3 illustrates an intrauterine system having a frame (1) with a concave triangular shape and rounded corners. The reservoir (2) is placed inside the frame at the bottom apex and both are pushed into a polymer or metal cup (8). The threads (3) are passed through the hole in the bottom of the cup and knotted as close to the frame as possible.
Figure 4:
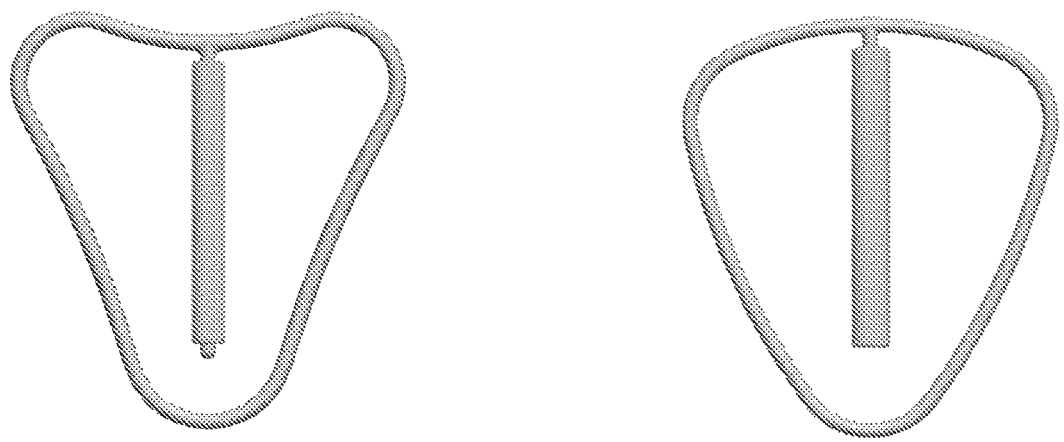
FIG. 4 illustrates further examples of different frames and reservoirs for the intrauterine systems according to the invention.
Figure 5:
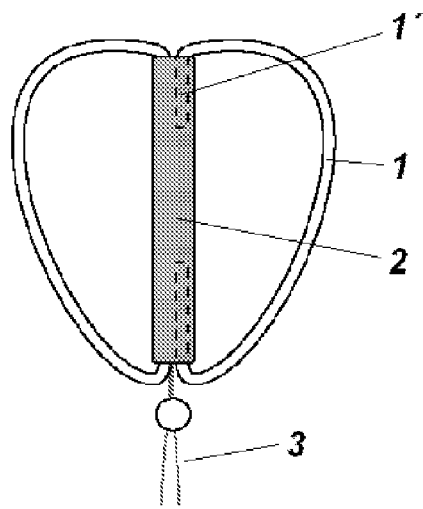
FIG. 5 illustrates an intrauterine system wherein the ends of an open frame or frame halves (1') are used to attach the reservoir (2) to the frame. The threads (3) for the removal of the system are attached either at the lower end of the frame or inserted through the reservoir and attached at the upper end of the reservoir or of the frame.
Figure 6:
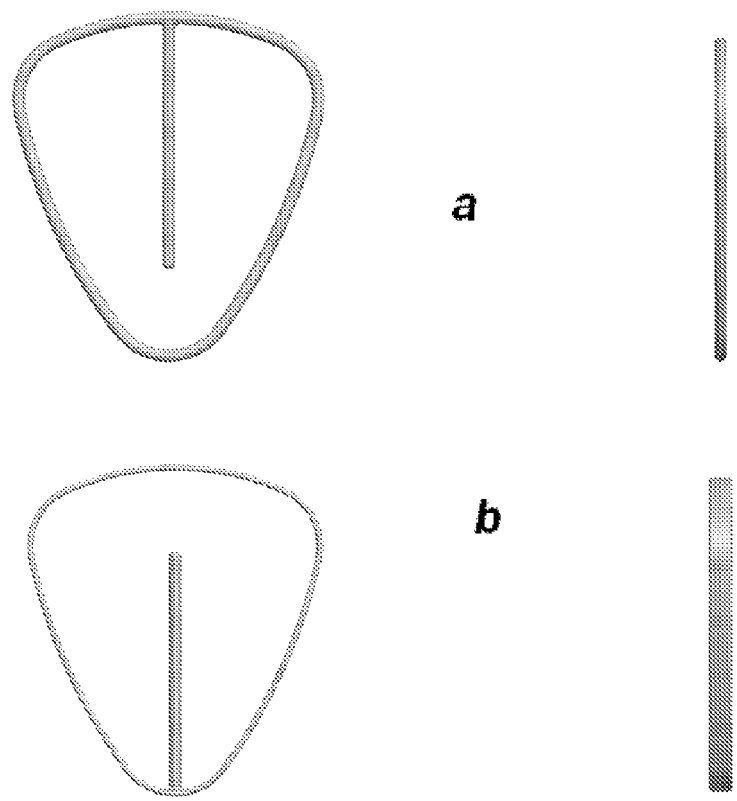
FIG. 6 illustrates a front and a side view of a triangular shaped intrauterine system having a frame with round cross section (FIG. 6a) and flat cross section (FIG. 6b).
Figure 7:
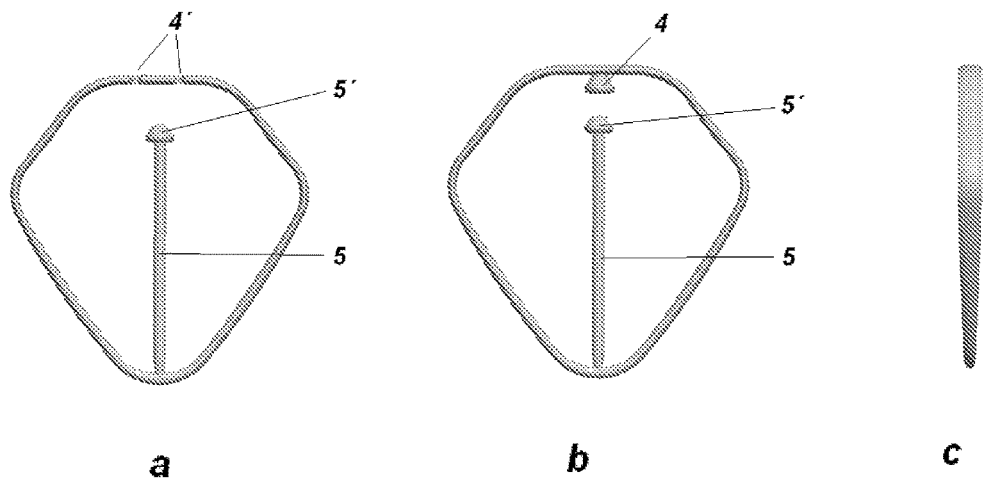
FIG. 7 illustrates front view of pentagonal frames (FIGS. 7a and 7b) and a side view of the same frames (FIG. 7c) showing local thinning at the lower part of the frame. Both frames have a shaft (5) connected to the bottom of the frame and a locking means (5') on the upper end of the shaft to retain the reservoir and prevent it from sliding off. The frame 7a has indentations (4') and the frame 7b an extension (4) on the upper part of the frame.
Figure 8:
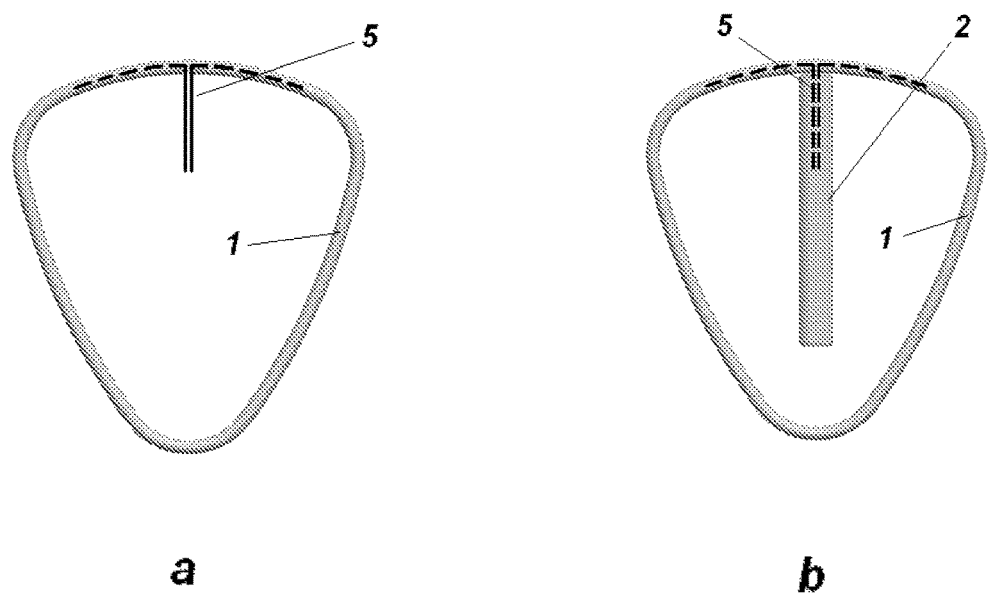
FIG. 8 illustrates a triangular shaped frame (1, FIGS. 8a and 8b) comprising a metal or polymer supporting means inside the frame (5). The ends of the supporting means are bent to form a pair of rod like extensions or shafts on which the reservoir (2) is assembled.

The object of the present invention is an intra-uterine system (IUS) for a relatively long-term insertion into a uterine cavity, and methods for manufacturing this type of intrauterine systems. The IUS according to the invention comprises a frame and a reservoir connected to the frame, wherein the frame forms a continuous, closed and flexible system of polygonal, preferably triangular or pentagonal, shape and wherein at least one end of the reservoir is connected to the inner surface of the frame and the reservoir comprises at least one therapeutically active substance. The reservoir connected to the frame gives the sufficient stiffness to the system, especially during the insertion step.

The frame comprises a thermoplastic polyurethane elastomer which is the reaction product of a) one or more aliphatic and/or cycloaliphatic diisocyanate with an isocyanate content of 32 to 75 weight-%, b) at least one polyol component having a number-average molecular weight Mn of from 501 to 10.000 g/mol and on average from 1.8 to not more than 3.0 Zerewitinoff-active hydrogen atoms, c) at least one low molecular weight polyfunctional alcohol component having a number-average molecular weight Mn of from 60 to 500 g/mol and on average from at least 1.8 to not more than 3.0 Zerewitinoff-active hydrogen atoms as chain extender, d) optionally monofunctional alcohols as chain terminators, in the presence of e) one or more catalysts, with the addition of f) from 0 to 35 wt.-%, based on the weight of the thermoplastic polyurethane made of components a) to d), of inorganic fillers, g) optionally, further additives and/or auxiliary substances in which the ratio of the isocyanate groups of a) to isocyanate-reactive groups of b), c) and optionally d) is from 0.9:1 to 1.1:1.

The most preferable aliphatic and/or cycloaliphatic diisocyanate a) is 1,6-hexamethylene diisocyanate or mixtures of 1,6-hexamethylene diisocyanate with other aliphatic and/or cycloaliphatic diisocyanates.

The most preferable polyol component b) is a polycarbonate polyol or a mixture of a polycarbonate polyol with a polyether and/or polyester polyol.

A preferable chain extender c) is a mixture of a straight chain oligomer, prepared from 1,6-hexanediol and ε-caprolactone, and hydroquinone bis(2-hydroxyethyl)-ether. Another preferable chain extender c) is selected from long chain aliphatic diols with more than 10 carbon atoms, such as 1,10-decanediol or 1,12-dodecanediol.

Another object of the present invention is to provide an intrauterine system, which is easy to insert and remove without causing any pain, is easy and comfortable to use and has a shape and size fitting to the size of the endometrial cavity thus minimizing or eliminating the possibility of expulsion and avoiding side effects, for example such as caused by the irritation of the endometrium.

A further object of the invention is an intra-uterine system, which has a safe and optimized design to avoid the perforations or penetrations of the uterine wall.

Still another object of the invention is a convenient and reliable method for delivering therapeutically active substances to a female mammal. The method involves the steps of preparing an intrauterine system having a continuous, closed and flexible frame of polygonal shape and a reservoir connected to the frame, wherein the frame comprises a thermoplastic polyurethane elastomer and the reservoir comprises at least one core comprising a polymer composition and a therapeutically active substance mixed therein, positioning and maintaining the intrauterine system in the uterus of the female mammal to be treated, and maintaining it there for a prolonged period of time, or at least for a time sufficient to deliver an effective amount of the substance to the female mammal.

A further object of the invention is a light-stable, thermoplastic polyurethane elastomer for intra-uterine systems with improved blooming behaviour and very good hydrolytic stability comprising the reaction product of a polycarbonate polyol or a mixture of a polycarbonate polyol with a polyether polyol and/or a polyester polyol, 1,6-hexamethylenediisocyanate and optionally additional (cyclo)aliphatic diisocyanates and at least one difunctional chain extender c1) with a number average molecular weight Mn of from 60 to 286 and optionally at least one chain extender c2) with a number average molecular weight Mn between 104 and 500 g/mol, which is different from the chain extender c1), corresponding to formula (I) or formula (II).

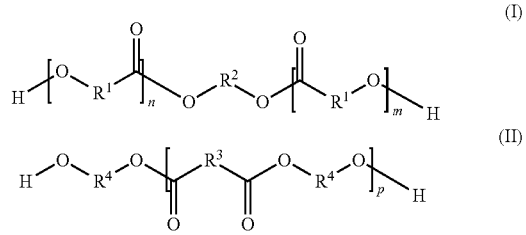

in which
R$^1$ represents a branched or unbranched alkylene radical with from 1 to 12 C atoms or a substituted or unsubstituted alkarylene radical with from 6 to 24 C atoms,
R$^2$, R$^4$ each represents a branched or unbranched alkylene radical with from 1 to 12 C atoms or an alkoxyalkylene radical with from 1 to 12 C atoms or a substituted or unsubstituted alkarylene radical with from 6 to 24 C atoms or a substituted or unsubstituted alkoxyarylene radical with from 6 to 24 C atoms,
R$^3$ represents a branched or unbranched alkylene radical with from 1 to 8 C atoms or a substituted or unsubstituted alkarylene radical with from 6 to 20 C atoms or a substituted or unsubstituted arylene radical with from 6 to 20 C atoms or a substituted or unsubstituted aralkylene radical with from 6 to 20 C atoms,
n, m each represent 0 to 10, where n+m≥1, and
p represents 1 to 10.

DETAILED DESCRIPTION OF THE INVENTION

The advantages of the invention are obtained by the intrauterine system as described above. The system comprises a frame and a reservoir connected to the frame, wherein the frame forms a continuous, closed and flexible system of polygonal shape and wherein at least one end of the reservoir is connected to the inner surface of the frame and the reservoir comprises at least one therapeutically active substance. The reservoir gives the sufficient stiffness to the intrauterine system during the insertion procedure and during the use. The frame is preferably triangular or pentagonal and comprises a thermoplastic polyurethane elastomer. The intrauterine system has an uncomplicated design and can be prepared by an economically attractive manufacturing process.

According to an embodiment, the invention provides an improved intrauterine system which is easy to insert and remove and is safe and comfortable to wear. The shape and size of the system are designed to fit to the size of the endometrial cavity and to avoid irritation of the endometrium, which usually would lead to various side effects and to discontinuation of the system.

According to another embodiment of the invention, the system has an optimized design and smooth shape to avoid the perforations or penetrations of the uterine wall.

The frame of the delivery system comprises a thermoplastic polyurethane elastomer obtainable from a polycarbonate polyol or a mixture of a polycarbonate polyol and a polyether and/or polyester polyol, 1,6-hexamethylene diisocyanate and optionally additional (cyclo)aliphatic diisocyanates and at least one difunctional chain extender with a number average molecular weight Mn of 60 to 286 and optionally at least one chain extender with a number average molecular weight Mn between 104 and 500 g/mol, which is different from the chain extender c1), corresponding to formula (I) or formula (II). The chain extender can preferably be a mixture of a straight chain oligomer, prepared from 1,6-hexanediol and ε-caprolactone, and hydroquinone bis(2-hydroxyethyl)-ether. The chain extender can preferably be also a long chain aliphatic diol, such as 1,10-decanediol or 1,12-dodecanediol. The frame is flexible and elastic but has still a relatively high degree of stiffness. The cross section thickness is sufficiently high to provide wanted resilience in use. However, the stiffness and the thickness are not so high as to prevent the frame from being bent through a substantial angle in use. Furthermore, the material has relatively high elasticity and characteristics which permit the frame to be deformed and then again to return to its original configuration upon release of the deforming force.

Flexible refers here to the ability of the frame to bend easily and to withstand stress and strain without being damaged or broken. Stress is the force applied per unit area of a cross-section that causes deformation. Strain is the elongation or increase in the length relative to its original length. For example, the frame of the present invention can be deformed or flexed easily, such as by applying pressure from opposite external sides of the frame. Upon relieving of the pressure the frame will return to its original shape. Flexibility is particularly important and useful for enhancing user comfort while inserting, using or removing the intrauterine system.

The frame has a shape and size designed and adapted for placing in the endometrial cavity. The frame has a continuous, curved shape, which differs from a full circle by being essentially polygonal, preferably pentagonal or triangular. The corners of polygonal frames are preferably slightly rounded. The frame may be coated by a polymer layer, a film or a membrane, said frame and polymer layer comprising the same or different polymer composition.

The cross section of the frame can have almost any smooth shape, and can be for example circular, semi-circular, rectangular, oval, flat, elliptical, star-shaped, angular, polygonal and the like. The cross section may also vary along the length of the frame by having localised thinning, for example at the corners of polygonal, such as triangular or pentagonal, frames to adjust or further reduce the stiffness of the frame. The optimal shape and cross-section of the frame will render the system fundus seeking. The term fundus seeking means that instead of causing the expulsion of the system or changing the position of the system, the forces caused by the uterus or uterine contractions will at most only slightly push the system upwards, the main tension being balanced by the movement or vibration of the flexible frame.

The frame may further comprise a supporting means, for example in a form of a core, fibre or wire, to reinforce the frame and/or to give additional flexibility to the frame. The supporting means can be made of any material which is inert and biologically compatible as long as it possesses sufficient strength and elasticity and remains unchanged for a sufficient period of time in the conditions prevailing in the uterus. Suitable stable biomedical materials for human use are well known in the art and include but are not limited to inert biocompatible metals, polymer composites, reinforced rubbers, flexible thermoplastic elastomers, such as ethyl vinyl acetate (EVA), thermoplastic polymers, such as styrene copolymers, for example styrene-isobutylene-styrene copolymer (SIBS) and styrene-butadiene-styrene copolymer (SBS), polyurethanes, thermoplastic urethane elastomers, thermoplastic polyurethane silicone elastomers, thermoplastic polyolefins, polyamides, polytetrafluoroethylene and polyethylenes. Biodegradable polymers can be used for contemporary supporting means.

The frame may also comprise means for attaching it into an inserter, for example a projection, a knob, a notch or an indentation.

The reservoir comprises at least one core comprising a polymer composition. Said one or each core may be encased by one or more polymer layers, either a membrane or a film. The length of the reservoir is preferably larger than the diameter or the width or height. The ends of the reservoir can be open or can be sealed by using for example an adhesive or the polymer composition of the membrane.

According to one embodiment of the invention the reservoir comprises one core encased by a polymer layer, either a membrane or a film, the core and the polymer layer essentially comprising the same or different polymer composition.

According to another embodiment of the invention the reservoir comprises two or more cores, each encased by a polymer layer, either a membrane or a film, said cores and polymer layers preferably comprising the same or different polymer composition.

According to still another embodiment of the invention, at least one of the cores of the reservoir comprises one or more therapeutically active agents to be delivered in the uterus.

The reservoir may have various sizes and shapes. Preferably the reservoir is a rod-like elongated element having for example circular, round, oval, flat, elliptical, rectangular, angular, polygonal or star-shaped cross section, and the like. The flat reservoir has a rectangular or essentially elliptical cross section. The corners or edges of the reservoir with rectangular, angular, polygonal or star-shaped cross section are preferably slightly rounded to avoid any sharp contact points which might irritate the uterus or reduce the wearing comfort. By choosing the flat shape the outer diameter of the reservoir and thus the dimensions of the inserter tube and/or the intrauterine system itself can be reduced. Reservoirs with unsymmetrical cross section, for example flat and rectangular reservoirs, can lie on the plane of the frame or perpendicular to that plane.

According to the embodiment in which the reservoir comprises two or more cores, said cores may be positioned next to each other, side-by-side, one on the other or within each other. The length and the diameter of the cores may be the same or different. The cores can be separated from each other by a separation membrane or by an inert placebo core. One or more of the cores can also be a rod, a wire or a thread consisting of an inert biocompatible metal or of polymer, the purpose of which is to give additional rigidity and durability to the reservoir, and/or to serve to anchor or join the reservoir onto the frame. Any combination of structure is naturally possible and within the scope of the invention.

The polymer layer, a membrane or a film, may fully cover the frame, the supporting means or the core, or cover only a part of them, whereby the degree of extension can vary depending on a number of factors, for example such as the choice of materials. The thickness of the polymer layer depends for example on materials used as well as on the intended use of the intrauterine system. The membrane or film may consist of more than one layer in which case each layer has a certain thickness, and the thickness of the layers may be the same or different.

The intrauterine system may comprise a thread attachment, i.e. one or more threads or strings which can be used to remove or locate the system, or to detect the presence of the system if expulsion is to be suspected. Threads can be attached to the frame by several ways for example depending on whether the reservoir is connected to the top or to the bottom of the frame. When the reservoir is connected to the upper part of the frame, the threads are attached for example to the bottom of the frame, to the lower end of the reservoir or to both. Alternatively the threads can go through the reservoir to the upper part of the frame. When the reservoir is connected to the lower part of the frame, the threads are attached for example to the bottom of the frame or the threads can go through the reservoir to its upper end. In case the reservoir comprises one or more cores in the form of a thread, these threads can also be used as strings to detect or remove the intrauterine system after use or when necessary.

The intrauterine system according to the invention, either the frame or the reservoir, or both, may further comprise at least one image enhancing means to facilitate the detection of the device without a physical intrusion into the area of the body wherein the device has been inserted. The means can be for example X-ray contrast agent, a ferromagnetic agent or an agent for the ultrasound or fluoroscopic imaging of the system.

Said image enhancing means are preferably selected from the group consisting of
a) an inert metal coating on at least part of the body of the intrauterine system;
b) inert metal inserts, clips, rings or sleeves fixedly positioned on the body of the intrauterine system;
c) metal or ferromagnetic powder or particles or suitable metal or alkali metal salts mixed during the compounding step in the raw materials of the frame, core matrix or membrane of the intrauterine system, and
d) a metallic cup, connector, adapter, clamp, sleeve, shaft or holder fixed at a suitable position on the frame, which can also be used to anchor or join the reservoir onto the frame.

The metal is preferably selected from the group consisting of inert metals, such as silver, gold, titanium, tungsten, bismuth, platinum, tantalum and palladium. Preferred metals are silver, gold, titanium and platinum, which are known to be compatible (i.e. physically inert) with the human body. However, copper may also be used.

Typically the thickness of the metal coating may vary from between about 0.1 nm and about 500 nm, preferably between about 1 nm and about 50 nm. However, even thicker coatings of about 0.1 mm are possible.

The metal clips, rings, sleeves or the like may be unembedded or at least partly embedded in the body of an IUS. Partial embedding of the metal parts smoothens the surface of the IUS while not yet impairing the sonographic visibility compared to unembedded counterparts. In case of rings it is advantageous to use double rings to enhance echogenicity. In case of clips and sleeves, the broader the clip or sleeve, the better is the visibility.

If metal powder, particles or salts are mixed with the raw materials of the frame, core matrix or membrane of an IUS during the compounding step, the amount of metal powder is typically from about 0.1 to about 25% by weight, preferably from about 1 to about 10% by weight of the raw materials.

The intrauterine system according to the invention has been designed for a relatively long-term insertion into a uterine cavity. However, a long-term insertion may vary greatly, for example from a couple of weeks to several years, the time being typically from one to ten years, preferably from 1 to 5 years.

According to the invention the frame of the intrauterine device comprises thermoplastic polyurethane elastomers which can be prepared using known methods from the above defined reactants comprising polyol, diisocyanate, chain extenders, and optionally monofunctional chain terminators, catalyst(s), conventional auxiliary substances and additives. Specifically, such thermoplastic polyurethanes have excellent resistance to hydrolysis, light, oxidative degradation, heat and the like. They also have excellent mechanical properties with respect to flexibility, low temperature properties and elastic recovery.

The polyol includes preferably for example polyether polyols, polyester polyols and polycarbonate polyols. As the polyol component b) there are used those having on average from at least 1.8 to not more than 3.0 Zerewitinoff-active hydrogen atoms and a number-average molecular weight Mn of from 501 to 10000. The polyols often contain small amounts of non-linear compounds resulting from their preparation. The term "substantially linear polyols" is therefore often used. The polyol component preferably consists of 100 to 50 mol-%, preferably 100 to 65 mol-% and more preferably 100 to 70 mol-% of at least one polycarbonate polyol with a number average molecular weight of from 501 to 3000 g/mol, preferably of from 1000 to 2500 g/mol and 0 to 50 mol % of a polyether and/or polyester polyol with a number average molecular weight of from 501 to 10000 g/mol, preferably 0 to 35 mol % of a polyether and/or polyester polyol with a number average molecular weight of from 501 to 6000 g/mol and more preferably 0 to 30 mol % of a polyether and/or polyester polyol with a number average molecular weight of from 700 to 4000 g/mol.

Polycarbonate polyol may be, for example, a polycarbonate polyol obtainable by ring-opening polymerization of an alkylene carbonate, by transesterification of a diol compound with a chloroformate, or by a reaction of a polyol with phosgene or a dialkyl carbonate or a diaryl carbonate. Dialkylcarbonate may be a C1-C4 alkylcarbonate such as, for example, dimethylcarbonate and diethylcarbonate. Suitable diols or diol mixtures comprise the polyhydric alcohols mentioned per se above in relation to the polyester polyols and having an OH functionality of 2 or more, for example such as 2-methylpropanediol, dipropylene glycol, 1,4-butanediol, 1,6-hexanediol, 3-methyl-1,5-pentanediol, neopentyl glycol, 1,5-octanediol, 1,4-bis-(hydroxymethyl)cyclohexane, and the like. Preferably the diols are 1,4-butanediol and 1,6-hexanediol and mixtures thereof.

Such polycarbonate polyols preferably have number average molecular weights of from 501 to 3000 g/mol, particularly preferably from 1000 to 2500 g/mol.

Polyether polyols may be homopolymers or copolymers of alkylene oxides including C2-C5-alkylene oxides such as, for example, ethylene oxide, propylene oxide, butylene oxide, tetrahydrofuran, and 3-methyltetrahydrofuran; homopolymers or copolymers of the above alkylene oxides obtained by using, as an initiator, water, C2-C40-polyols, such as ethylene glycol, propylene glycol, 12-hydroxystearyl alcohol and hydrogenated dimerdiol; and abducts of the above alkylene oxides with bisphenol-A or hydrogenated bisphenol-A. These polyether polyols may be used alone or in combination of two or more. Specific examples are polyoxyethylene glycol, polyoxypropylene glycol, polyoxytetramethylene glycol, polyoxyethylene polyoxytetramethylene glycol, polyoxypropylenepolyoxytetra methylene glycol, and polyoxyethylene polyoxypropylene polyoxytetramethylene glycol. The linear polyether diols have number-average molecular weights Mn of from 501 to 6000, preferably 700 to 4000. They can be used either individually or in the form of mixtures with one another.

Suitable polyester polyols can be prepared, for example, from dicarboxylic acids having 2 to 12 carbon atoms, preferably 4 to 6 carbon atoms, and polyhydric alcohols. There come into consideration as dicarboxylic acids, for example aliphatic dicarboxylic acids, such as succinic acid, glutaric acid, adipic acid, suberic acid, azelaic acid and sebacic acid, or aromatic dicarboxylic acids, such as phthalic acid, isophthalic acid and terephthalic acid. The dicarboxylic acids can be used individually or in form of mixtures, for example in form of a succinic, glutaric and adipic acid mixture. Examples of polyhydric alcohols are glycols having from 2 to 12, preferably 2 to 6, carbon atoms, for example ethylene glycol, diethyllene glycol, 1,4-butanediol, 1,5-pentanediol, 1,6-hexanediol, 1,8-octanediol, 1,10-decanediol, 1,12-dodecanediol, 2,2-dimethyl-1,3-propanediol, 1,3-propanediol or dipropylene glycol. Depending on the desired properties, polyhydric alcohols can be used on their own or in the form of a mixture with one another. Also suitable are esters of carboxylic acids with the mentioned diols, such as 1,4-butanediol or 1,6 hexanediol, condensation products of w-hydroxycarboxylic acids, such as ω-hydroxycapronic acid, or polymerization products of lactones, for example ε-caprolactone or optionally substituted ω-caprolactones. There are preferably used as polyester diols ethandiole polyadipates, 1,4-butanediol polyadipates, ethanediol-1,4-butanediol polyadipates, 1,6-hexanediol polyadipates, 1,6-hexanediol-neopentyl glycol polyadipates, 1,6-hexanediol-1,4-butanediol polyadipates and polycaprocatones. The polyester diols have number-average molecular weights Mn of from 501 to 10000, preferably 700 to 4000 and can be used individually or in the form of mixtures with one another.

Polyisocyanates used in the present invention may be, for example, aliphatic diisocyanates or a mixture of aliphatic diisocyanates, preferably mixtures of 1,6-hexamethylenediisocyanate.

Examples of suitable diisocyanates include aliphatic diisocyanates selected for example from the group consisting of trimethylene diisocyanate, 1,4-tetramethylene diisocyanate, 1,6-hexamethylene diisocyanate, 2,2,4- and/or 2,4,4-trimethylhexamethylene diisocyanate, decamethylene diisocyanate, ethylene diisocyanate, ethylidene diisocyanate, propylene-1,2-diisocyanate, cyclohexane-1,4-diisocyanate, 4,4'-dicyclohexylmethane diisocyanate and the isomeric cyclohexanedimethylene diisocyanates, isophorone diisocyanate, and mixtures thereof.

The use of 1,6-hexamethylene diisocyanate is preferred.

The chain extenders c) may be aliphatic, cycloaliphatic, or aromatic and are exemplified by diols, including polyester diols, polyether diols and polycarbonate diols, diamines and amino alcohols. The chain extender is preferably, for example, a diol such as 1,2-ethanediol, 1,3-propanediol, 1,4-butanediol, 1,6-hexanediol, 1,8-octanediol, 1,10-decanediol, 1,12-dodecanediol or hydroquinone bis-2-hydroxyethyl ether (HQEE). 1,8-octanediol, 1,10-decanediol, 1,12-dodecanediol and hydroquinone bis-2-hydroxyethyl ether (HQEE) are preferred. 1,12-dodecanediol and hydroquinone bis-2-hydroxyethyl ether (HQEE) are particularly preferred. In the present invention, mixtures of a straight chain oligomer, prepared from 1,6-hexanediol and ε-caprolactone, and hydroquinone bis-2-hydroxyethyl ether (HQEE) are also particularly preferred.

Monofunctional alcohols or amines can optionally be used as a chain terminator d).

Catalysts are preferably used in the polyurethane reaction mixtures. Any of the catalysts conventionally employed or known in the art and to the literature to catalyze the reaction of an isocyanate with a reactive hydrogen containing compound can be employed for this purpose. Such catalysts particularly include organic and inorganic acid salts of, and organometallic derivatives of bismuth, tin, iron, antimony, cobalt, thorium, aluminum, zinc, nickel, cerium, molybdenum, vanadium, copper, manganese and zirconium, as well as phosphines and tertiary organic amines. Representative catalysts include for example sterically hindered bismuth catalysts, for example such as bismuth-neodecanoate, bismuthoctoate or bismuth carboxylate (BiCat), tin compounds such as stannous diacetate, stannous dioctoate, stannous dilaurate, or the dialkyltin salts of aliphatic carboxylic acids, e.g. dibutyltin diacetate, dibutyltin dilaurate, dibutyltin dioctoate, titanic esters, iron compounds, e.g. ferric acetylacetonate or the like. The amounts of the catalysts usually used are from 0.0001 to 0.5 part by weight per 100 parts by weight of polyhydroxy compound (b).

Besides catalysts, conventional auxiliaries may also be added to the structural components, including for example surface-active substances, flame retardants, nucleating agents, antioxidants, coatings, coloring materials, preservatives, lubricants, and mold-release agents, dyes, and pigments, and, if appropriate, stabilizers, e.g. with respect to hydrolysis, light, heat, or discoloration, inorganic and/or organic fillers, material, which can for example be used for identification or detection of the intrauterine system, such as metallic or magnetic particles or an X-ray contrast medium like barium sulphate, reinforcing agents, and plasticizers.

Examples of suitable UV light stabilizers which may be used include by way of non-limiting example Tinuvin® 144, Tinuvin® 234, Tinuvin® 328, Tinuvin® 765, Tinuvin® 770, all of which are commercially available. Among the commercially available anti-oxidants which are considered useful are UVINUL® A03 and IRGANOX® 1010, IRGANOX® 1035, IRGANOX® 1076, IRGANOX® 1098 and IRGANOX® 1222. A suitable commercially available anti-oxidant and metal deactivator is IRGANOX® MD 1024.

The polyurethane elastomer of the present invention can be prepared by reacting a polycarbonate diol with a diisocyanate compound and chain extenders in the presence of a catalyst and optionally fillers and optionally in the presence of an antioxidant and/or a curing agent and other additives, if the case requires. In addition a suitable lubricant or a mold release agent can be used. A known method selected from a one-shot method, a prepolymer method, etc. can be employed.

According to a preferred embodiment, the thermoplastic polyurethane elastomer is made by reacting a polycarbonate diol, prepared from 1,6-hexanediol and dimethyl carbonate and having a number average molecular weight of from 501 to 3000 g/mol, preferably of from 501 to 2500 g/mol and more preferably of from 1000 to 2500, with 1,6-hexamethylenediisocyanate, a mixture of a straight chain oligomer, prepared from 1,6-hexanediol and ε-caprolactone, and hydroquinone bis(2-hydroxyethyl)ether as chain extender. Another preferred thermoplastic polyurethane elastomer is made by reacting a polycarbonate diol, prepared from 1,6-hexanediol and dimethylcarbonate and having number average molecular weights of from 501 to 3000 g/mol, preferably of from 501 to 2500 and more preferably of from 1000 to 2500 g/mol with 1,6-hexamethylenediisocyanate and 1,12-dodecanediol as chain extender.

One embodiment of the invention therefore is a light-stable, thermoplastic polyurethane elastomer comprising the reaction product of
a) one or more aliphatic and/or cycloaliphatic diisocyanate with an isocyanate content of 32 to 75 weight-%,
b) at least one polyol component having a number-average molecular weight Mn of from 501 to 10.000 g/mol and on average from 1.8 to not more than 3.0 Zerewitinoff-active hydrogen atoms,
c) at least one low molecular weight polyfunctional alcohol component having a number-average molecular weight Mn of from 60 to 500 g/mol and on average from at least 1.8 to not more than 3.0 Zerewitinoff-active hydrogen atoms as chain extender,
d) optionally monofunctional alcohols as chain terminators, in the presence of
e) one or more catalysts,
with the addition of
f) from 0 to 35 wt.-%, based on the weight of the thermoplastic polyurethane made of components a) to d), of inorganic fillers,
g) optionally, further additives and/or auxiliary substances in which the ratio of the isocyanate groups of a) to isocyanate-reactive groups of b), c) and optionally d) is from 0.9:1 to 1.1:1.

In one embodiment, the thermoplastic polyurethane elastomer comprises the reaction product of
a) an isocyanate component comprising:
a1) from 50 to 100 mol-% of 1,6-hexamethylene diisocyanate and
a2) from 0 to 50 mol-% of an aliphatic diisocyanate other than 1,6-hexamethylene diisocyanate or a mixture of aliphatic and/or cycloaliphate diisocyanates which does not include 1,6-hexamethylene diisocyanate,
b) a polyol component comprising:
b1) from 50 to 100 mol-% of at least one polycarbonate diol with a number average molecular weight of from 501 to 3000 g/mol and,
b2) from 0 to 50 mol-% of a polymeric diol other than a polycarbonate diol with a number average molecular weight of from 501 to 6000 g/mol, c) a chain extender component comprising: at least one difunctional chain extender selected from the group comprising chain extenders having a number average molecular weight of from 90 to 286 g/mol and reaction products of these difunctional chain extenders with ε-caprolacton or difunctional carboxylic acids, said reaction products corresponding to the formula (I) or formula (II) as defined above,
d) optionally monofunctional alcohols as chain terminators,
in the presence of
e) one or more catalysts,
with the addition of
f) from 0.1 to 35 wt.-%, based on the weight of the thermoplastic polyurethane made of components a) to d), of inorganic fillers,
g) optionally, further additives and/or auxiliary substances
in which the ratio of the isocyanate groups of a) to isocyanate-reactive groups of b), c) and d) is from 0.9:1 to 1.1:1.

Preferably, the thermoplastic polyurethane elastomer comprises the reaction product of
a1) from 65 to 100 mol-% of 1,6-hexamethylene diisocyanate and
a2) from 0 to 35 mol-% of an aliphatic diisocyanate other than 1,6-hexamethylene diisocyanate or a mixture of aliphatic and/or cycloaliphate diisocyanates which does not include 1,6-hexamethylene diisocyanate,
b) a polyol component comprising:
b1) from 65 to 100 mol-% of at least one polycarbonate diol with a number average molecular weight of from 501 to 3000 g/mol and,
b2) from 0 to 35 mol-% of a polyether diol and/or a polyester diol with a number average molecular weight of from 501 to 4000 g/mol,
c) a chain extender component comprising:
c1) from 35 to 100 mol-% of at least one difunctional chain extender having a number average molecular weight of from 118 to 286 g/mol and
c2) from 0 to 65 mol-% of a chain extender with a number average molecular weight between 104 and 500 g/mol, which is different from the chain extender c1), corresponding to the formula (I) or formula (II) as defined above,
d) optionally monofunctional alcohols as chain terminators,
in the presence of
e) one or more catalysts,
with the addition of
f) from 0.1 to 35 wt.-%, based on the weight of the thermoplastic polyurethane made of components a) to d), of inorganic fillers,
g) optionally, further additives and/or auxiliary substances
in which the ratio of the isocyanate groups of a) to isocyanate-reactive groups of b), c) and d) is from 0.9:1 to 1.1:1.

In a still further preferred embodiment, the thermoplastic polyurethane elastomer comprises the reaction product of
a) an isocyanate component comprising:
a1) from 70 to 100 mol-% of 1,6-hexamethylene diisocyanate and
a2) from 0 to 30 mol-% of an aliphatic diisocyanate other than 1,6-hexamethylene diisocyanate or a mixture of aliphatic and/or cycloaliphate diisocyanates which does not include 1,6-hexamethylene diisocyanate,
b) a polyol component comprising:
b1) from 70 to 100 mol-% of at least one polycarbonate diol with a number average molecular weight of from 1000 to 2500 g/mol and,
b2) from 0 to 30 mol-% of a polyether diol and/or a polyester diol with a number average molecular weight of from 600 to 4000 g/mol,
c) a chain extender component comprising:
c1) from 35 to 95 mol-% of at least one difunctional chain extender having a number average molecular weight of from 146 to 286 g/mol and
c2) from 5 to 65 mol-% of a chain extender with a number average molecular weight between 104 and 500 g/mol, which is different from the chain extender c1), corresponding to the formula (I) or formula (II) as defined above,
d) optionally monofunctional alcohols as chain terminators, in the presence of
e) one or more catalysts,
with the addition of
f) from 0.1 to 35 wt.-%, based on the weight of the thermoplastic polyurethane made of components a) to d), of inorganic fillers,
g) optionally, further additives and/or auxiliary substances
in which the ratio of the isocyanate groups of a) to isocyanate-reactive groups of b), c) and d) is from 0.9:1 to 1.1:1.

Polymer compositions of the core, the membrane and the possible separation membrane or the inert placebo compartment, can be the same or different and may stand for one single polymer or a polymer composition, or may be made up of polymers that are blended with each other. In principle any polymer, either biodegradable or non-biodegradable, can be used as long as it is biocompatible. Further, the intrauterine system should retain structural integrity during the length of intended period of use.

Suitable materials are naturally occurring or synthetic materials, preferably materials that are biologically compatible with body fluids, and uterine tissues, and essentially insoluble in body fluids with which the device will come in contact. The use of rapidly dissolving materials or materials highly soluble in natural body fluids is to be avoided since the system is aimed to remain in place for prolonged periods of time.

A preferred polymer composition comprises siloxane based elastomer, thermoplastic polyurethane, thermoplastic polyurethane elastomer, EVA, thermoplastic polyurethane silicone elastomer or a mixture of at least two of them.

The structural integrity of the material may be enhanced by the addition of a particulate material such as silica or diatomaceous earth. The elastomers can also be mixed with other additives to adjust elastomer's hydrophilic or hydrophobic properties while taking into account that all additives need to be biocompatible and harmless to the patient. The core or membrane may also comprise additional material to further adjust the release rate of one or several therapeutic substances, for example complex forming agents such as cyclodextrin derivatives to adjust the initial burst of the substance to the accepted or desired level or a fatty acid ester, preferably one containing from 2 to 20 carbon atoms. Auxiliary substances, for example such as tensides, antifoaming agents, stabilizers, solubilisers or absorption retarders, or a mixture of any two or more of such substances, can also be added in order to impart the desired physical properties to the body of the delivery system. Further, additives such as pigments, glossing agents, matting agents, colorants, mica or equal can be added to the body of the delivery system or the membrane or to both in order to provide the delivery system with a desired visual appearance. In addition, the polymer matrix may comprise other material, which can for example be used for identification or detection of the intrauterine system, such as metallic or magnetic particles or an X-ray contrast medium like barium sulphate.

Any suitable design of the delivery system or any combination of structure is naturally possible and within the scope of the invention.

Insertion forces of intrauterine devices (IUDs) and systems (IUSs) have been found to depend on the material and dimensions of the device, design characteristics such as the contour of the leading edge, and on the inserter design, dimensions and material properties. The forces caused by the removal process of the device have been observed to depend on the dimensions, flexibility and design of the IUS. These forces can be translated into pain during insertion and removal as well as into wearing comfort during the use of the system. Furthermore, the dimensions and material of the IUS are also believed to affect the wearing comfort of the IUS when it is placed in the uterus. In addition, a optimized size of an IUD relative to the uterine cavity is associated with decreased risk of complications, such as expulsion of the IUD or abnormal bleeding.

To test the properties of the intrauterine systems and to provide scientific basis for evaluating and developing optimal construction and design of these systems in order to achieve maximum wearing comfort and appropriate positioning of the system in the uterus, computer assisted virtual modelling was used and relevant functional laboratory test models were developed.

The model with typical female pelvic anatomy, including material features which give the tactile feed-back similar to that from in vivo situation, was designed and manufactured by moulding the inner parts by using appropriate polymers to give as realistic sensation as possible. Interchangeable cervix and uterus elements having different sizes and shapes, as well as a variety of positions (anteversion, retroversion) were used to adjust and exchange the anatomy and to allow simulation of the full range of female pelvic anatomy. Also the flexion, i.e. the hinge region between the uterine cervix and the uterine body, could be adjusted to allow comparison of insertion and removal forces representing the pain during these procedures, respectively.

With the test models typical anatomical features that impact the device's critical features in terms of insertion and removal forces as well as forces exerted from being placed in situ in the uterus could be simulated. Test models also made possible to allow modifications to simulate extreme anatomical situations, and to compare the properties and behaviour of these systems to the existing intrauterine devices and intrauterine systems. The models also enabled in-vitro set up for repeatable relative attribute testing with the possibility to include animal tissue for absolute testing.

The pressure caused by the intrauterine system on the uterus walls and the cervix was evaluated by using laboratory test model and computer assisted virtual modelling. Correct positioning and the tendency to expulsion can be deduced based on the relative forces the system exerts on the fundus, uterine walls and cervix.

Experiments done with laboratory test models confirmed that insertion forces did primarily depend on the dimensions, design characteristics and on material properties of the intrauterine system. The forces needed for the removal of the intrauterine system, representing the propensity of the system to expulsion, depend on the dimensions, flexibility and design of the IUS.

The intrauterine systems according to present invention have a body with blunt surfaces and gentle curves without any sharp features which would cause uterine injury. Therefore they especially fulfil the requirements for an ideal intrauterine system.

According to the invention, the intrauterine systems having a continuous, closed frame were found to exert relatively low pressures, suggesting that these are more comfortable than most existing intrauterine devices and systems. Intrauterine systems having for example more natural uterus shaped frame appear in the simulation tests to be fundus seeking as opposed to the systems having essentially round shaped frames. Especially polygonal such as triangular and pentagonal, as well as shield shaped and almond shaped frames, i.e. those frames which taper towards the cervix generally exert a greater proportion of overall force on the fundus, thus having a very low or no tendency to expulsion. In addition, these frames have reduced projection into uterotubal junctions and therefore do not irritate uterine walls at all.

Rounder shapes which have a tendency to extend or elongate downwards or in both directions and exert pressure on the cervix, have higher tendency to expulsion. The size of the intrauterine system is naturally an important factor. Polygonal frames having rounded corners, for example almond and shield, which were intentionally modelled too large for the uterus, have a propensity to elongate and apply pressure to both the fundus and the cervix. Some fundus seeking frames, although they do not exert pressure on the cervix, may apply a high force on the upper uterus walls, especially if the upper part of the frame is very rigid or relatively large. This problem impairing compliance properties can be overcome by optimizing the size of the frame and selecting suitable material for the frame. A flatter cross section of the polygonal frame, as opposed to substantially round cross section, tend to increase the device memory and the opening force and give also rise to lower pressures on the uterus suggesting that a design based on this shape could exhibit both fundus seeking and high compliance properties. Further, variable cross section of the frame, for example with localised thinning at the corners of a polygonal frame can be used to reduce stiffness.

Manufacturing Methods

The intrauterine systems in accordance with the invention can be prepared by methods well known in the art. A variety of thermoplastic processing techniques may be used including for example extrusion techniques, such as extrusion, co-extrusion, multi-layer extrusion, multi-lumen extrusion, and so on, and molding techniques, such as rotational molding and injection molding including co-injection or sequential injection molding technology, laminar injection molding, where multilayer structures are desired, compression or any other appropriate methods known in the art. The desired geometry of the intrauterine system can be achieved by using appropriately sized and shaped moulds or extrusion dies. The frame and the reservoir may be manufactured separately followed by their assembly, simultaneously or sequentially.

Injection molding of one or more polymeric materials can be used to efficiently produce a frame, a reservoir comprising a membrane and a core, optionally containing an active agent, or a complete intrauterine system comprising a frame and a reservoir. The polymer composition may be injected into a mold cavity of desired shape sequentially with one or more injection nozzles or syringes, or simultaneously by using a co-injection nozzle having two axially symmetric openings. The mold may be capable of producing more than one article in a given injection cycle by the use of multiple mold cavities. The molds and mold designs are well known in the art, and may be selected or adapted to produce the desired physical shape of the product.

Another preferred method of manufacture comprises extrusion. Selected polymer composition is extruded through a suitable die to form a rod-like or tube-like extrudate having desired diameter and shape of the cross section. The fibre is cut into pieces having an appropriate length required to form the frame, the reservoir or the supporting means for the frame, each having a desired size and shape. The pieces may then be assembled in any manner by using different methods suitable for this purpose, for example by placing the piece or pieces in a mould which has a desired form to produce a rod-like reservoir having one or more cores, or a continuous closed frame described above. The ends of the extruded pieces can be appropriately joined together by using a coupling means, if needed.

The coupling means can be any method, mechanism, device or material known in the art for bonding materials or structures together. Exemplary coupling means include for example injection molding, welding techniques, such as the hot-gas welding technique well known in the art, solvent bonding, adhesive joining, use of a layer of uncured, cross linkable elastomer forming composition, heat fusing, heat bonding, pressure, and the like. When manufacturing the frame, the polymeric substance must be sufficiently pliable when dry to allow the rods to be bent and formed into the final shape of the frame.

Tubular frame elements can also be joined into a closed system by using a plug or a stopper made of an inert, biocompatible material. Examples of suitable material are metals, such as gold, silver or silver alloys, tantalum, platinum, glass or ceramic material or any suitable polymers. If desired, a biocompatible adhesive can be used for better sealing or better adhesion of the plug or stopper to the frame element.

The polymer layer, a membrane or a film, can be applied onto the frame, core or the set of cores according to known methods such as by using extrusion or injection moulding methods, coating, spraying or dipping. Discontinuous coating can be used to produce reservoirs with sealed ends. As an alternative, the prefabricated membrane tube can be used. The tube is first expanded mechanically for example with a suitable device or by using for example pressurized gas, such as air, or by swelling the tube in a suitable solvent, such as cyclohexane, diglyme, isopropanol, or in a mixture of solvents, where after the swollen membrane tube is mounted onto the core. When the solvent evaporates, the membrane tightens on the core.

The reservoirs comprising several cores or the frame element consisting of more than one segment, can also be prepared for example by using a coextrusion method described in the Finnish patent FI 97947. Polymer or polymer composition is processed to the desired shape and size by using known extrusion methods. The membrane layer may then be applied onto the prefabricated suitably sized cores by feeding each of the cores to the extruder followed either by another core or by an empty space filled with air, which during the extrusion process will be filled with the membrane material.

The support means can be of solid material or hollow and can be prepared in a similar way.

The reservoir can practically be at any point inside the frame, at least one end of the reservoir being connected to any point on the inner surface of the frame by using several alternative methods. To achieve a simple insertion, the reservoir is preferably attached to the upper or lower part of the frame, or to both parts. The frame or the reservoir comprises retention or locking means to fix and retain the reservoir and to prevent it from sliding off.

The reservoir can be fixed on the frame by using different methods. The frame may for example comprise an elongated extension in the form of a metal or polymer shaft, core, rod or pin or the like at a suitable point on which the hollow tube-like reservoir is assembled, preferably by first enlarging the diameter of the reservoir tube to some degree, for example by using pressure or solvent swelling, and thereafter by simply sliding the reservoir onto the extension or inserting the extension into the hollow reservoir. The extension is preferably flexible in order to facilitate the assembly of the reservoir on it. After the reservoir has been assembled, the free end of the elongated extension may be for example heat formed to create a physical retention feature to mechanically retain the reservoir and prevent it from sliding off. To keep the reservoir in place the extension may also comprise a suitably shaped locking means or a stopper, over which the swollen reservoir is inserted.

The frame may also comprise a metal or polymer supporting means which is bent at the ends to form rod-like extensions on which the reservoir is assembled or molded. The ends of an open frame or frame halves can be inserted into the reservoir to join the reservoir and the frame together thus simultaneously forming the intrauterine system having a continuous closed frame. The ends of an open frame can also be bent to form extensions, on which the reservoir is assembled or molded. Further, the reservoir can be manufactured by coating the extension with a polymer layer, containing a therapeutically active substance, by using injection molding, dipping, spraying and like.

Other methods to attach the reservoir to the frame include for example known techniques of welding, use of an adhesive, or use of special metal or polymer inserts, clips, connectors, adapters, clothespin-type means or clamps or like. The intrauterine system can also be manufactured by using a metal or polymer cup, plug or sleeve which mechanically retains the reservoir, the threads and the frame or the ends of an open frame element. The cup, plug or sleeve could be rifled on the inner surface to reduce 'stiction' and to allow easier detachment. In this case threads preferably protrude through the base of the cup. These methods are especially suitable to be used with solid reservoirs, i.e. reservoirs not having a hollow, tube-like structure. A complete intrauterine system can further be manufactured by using for example injection molding techniques.

The frame according to the invention can principally be manufactured in any size as required. For optimal performance and wearing comfort the exact size depends on the mammal and particular application, and the size should be such that the system would not have a tendency to move or rotate inside the average sized uterine cavity. For human female an outer diameter of the frame is typically from 18 to 42 mm, preferably from 20 to 38 mm or from 22 to 36 mm. The cross sectional diameter is typically from 0.5 to 10 mm, preferably from 1 to 6 mm and more preferably from about 1.5 to 4 mm.

The dimensions of the reservoir depend on the application in which the intrauterine system is to be used. The dimensions of a drug containing delivery system depend on the expected release rate of the therapeutically active substance and the expected life-time of the intrauterine system. Typically the outer diameter of the reservoir, or the height and the width in case of a flat or a rectangular reservoir, may vary from 0.5 to 5 mm, preferably from 1 to 3.5 mm. If the reservoir is manufactured by coating methods, the wall thickness can be from 0.01 to about 5 mm, preferably from 0.2 to 3.5 mm. The length of the reservoir may vary from 0.5 mm up to the internal diameter of the frame, preferably from 15 to 36 mm.

The thickness of the polymer layer, the membrane or the film, encasing the core is such that it can be manufactured within acceptable tolerances by methods known in the art and conveniently lies within the range of from 0.01 to 1.0 mm, preferably from 0.1 to 0.6 mm. The thickness of a polymer layer separating the cores can be about from 0.01 to 5 mm.

The intrauterine delivery systems in accordance with the invention can be manufactured aseptically or can be sterilized by using known methods, for example by using physical, chemical or technical sterilization.

The frame is preferably manufactured by injection molding using known methods and tools having suitable shape and size. The reservoir according to the present invention can be easily fabricated in accordance with standard techniques. Once the polymer composition of core or cores has been selected, the desired shape of the reservoir is achieved for example by molding, casting extrusion, or by other appropriate processes. When the core material comprises polymers such as silicone elastomers, an additional curing step may be necessary. The membrane or film layer is then applied to the thus shaped core by using an appropriate method discussed above, e.g., by swelling a prefabricated polymer tube in a suitable solvent or by using mechanical stretching, placing it over the core and allowing the polymer to dry in place, or by dipping, wrapping, spraying, laminating or according to other known techniques.

A therapeutically active substance in a finely ground or even micronized form will be mixed in the polymer material of the core prior to processing to achieve a substantially uniform dispersion. A person skilled in the art is readily able to choose the geometry of the device and the polymer composition so that the desired daily release of the at least one pharmacologically active agent is achieved, and to determine the amount of the therapeutically active agent needed for each specific application and for the desired time of duration. Here the term "geometry" of the device primarily and specifically encompasses the overall dimensions and shape of the reservoir, i.e. the cross-sectional diameter, or the height and the width, as well as the length.

A variety of different therapeutically active or prophylactic substances can be used in conjunction with the invention. By "therapeutically active substance" is meant any substance or a salt, an ester or a prodrug thereof which by administration in the uterus is capable of defending against, or treating, a disease state in the human or animal body. By "prophylactic substance" is meant any substance (or its salt or prodrug) effective in defending against a disease state in the human or animal body, preferably the human body. The active substance(s) may be hydrophilic or lipophilic material(s).

Suitable therapeutically active or prophylactic substances for use in the present invention include, but are not limited to, the following: hormones, steroids, contraceptive drugs, drugs for hormone replacement therapy, selective androgen receptor modulators (SARM), drugs for the treatment of premenstrual syndrome, drugs for the treatment of endometriosis, drugs for the treatment of uterine fibroids (uterine leiomyomata and leiomyosarcoma), drugs for cervical ripening/induction of labour, selective estrogen receptor modulators (SERMs), selective progestin receptor modulators (SPRM), antimalarial substances, osteoporosis drugs, antiprogestins, aromatase inhibitors, bone active substances, anti-urinary incontinence substances, serotonin reuptake inhibitors (SSRIs), drugs for genitourinary disorders, anti-emetic drugs, 5HT3 antagonists, anti-angiogenesis factors, growth factors, enzymes, anesthetics, analgesics, anticoagulants and thrombolytic substances, anti-inflammatory substances, antimicrobials, anti-protozoal substances, antiviral substances, neuroleptic and antipsychotic drugs, opiate antagonists and agonists, anti-fibroid substances, antihypertensives, angiotensin inhibitors, anti-protozoal substances, anti-addiction drugs, anti-angiogenesis factors, anti-bacterial substances, anticancer chemotherapeutic substances, antifungals, antioxidants, diuretics, drugs for the central nervous system, fibrinolytic substances, free radical scavengers, gene therapy substances, growth factors, neurotrophic factors, peptides, photodynamic therapy substances, proteins, symphatomimetic substances, thrombin inhibitors, thrombolytic substances, and a combination of at least two thereof.

Therapeutically active substances especially suitable for use in the present invention include gestagenes selected from the group of levonorgestrel, norgestimat, norelgestromin, norethisteron, dydrogesteron, drospirenon, 3-beta-hydroxydesogestrel, 3-ketodesogestrel (=etonogestrel), 17-deacetylnorgestimat, 19-norprogesteron, acetoxypregnenolon, allylestrenol, amgeston, chlormadinon, cyproteron, demegeston, desogestrel, dienogest, dihydrogesteron, dimethisteron, ethisteron, ethynodioldiacetat, fluorogestonacetat, gastrinon, gestoden, gestrinon, hydroxymethylprogesteron, hydroxyprogesteron, lynestrenol (=lynoestrenol), mecirogeston, medroxyprogesteron, megestrol, melengestrol, nomegestrol, norethindron (=norethisteron), norethynodrel, norgestrel (including d-norgestrel and dlnorgestrel), norgestrienon, normethisteron, progesteron, quingestanol, (17alpha)-17-hydroxy-11-methylen-19-norpregna-4,15-dien-20-yn-3-on, tibolon, trimegeston, algeston acetophenid, nestoron, promegeston, 17-hydroxyprogesteronester, 19-nor-17hydroxyprogesteron, 17alpha-ethinyl-testosteron, 17alpha-ethinyl-19-nor-testosteron, d-17beta-acetoxy-13beta-ethyl-17alpha-ethinyl-gon-4-en-3-onoxim, tanaproget, or estrogenes selected from the group ethinylestradiol, mestranol, quinestranol, estradiol, estron, estran, estriol, estetrol, conjugated equine estrogenes.

The amount of the therapeutically active substance incorporated in the reservoir of the delivery system varies depending on the particular therapeutically active substance, the desired therapeutic effect and the time for which the system is expected to provide therapy. Reservoirs with varying sizes and shapes can be formulated for administering dosages for different therapeutical areas. The upper limit on the amount of therapeutically active substance depends on the size of the reservoir. The lower limit depends on the activity of the therapeutically active substance and on the expected release time. A person skilled in the art is readily able to determine the amount of the therapeutically active substance needed for each specific application of the delivery system. Preferably, the amount of therapeutically active substance varies between almost zero to 70 wt-%, when it is mixed into the polymer composition, the preferred amount being between 20-60 wt-%. Other possible ranges of the amount of the therapeutically active substance are 0.5-70 wt-%, 5-65 wt-%, 10-50 wt-%, 25-70 wt-%, 50-60 wt-% and 40-50 wt-%.

Based on the above, a further object of the invention is a method for manufacturing an intrauterine system having a closed continuous frame and a reservoir connected to the frame, said method comprising of injection molding, extruding or compressing the frame and the reservoir by using a sequential process comprising the steps of preparing the frame, preparing the first composition comprising a therapeutically active agent and a polymer composition to provide a core, preparing the second composition comprising a polymer composition to provide a membrane encasing the core, combining the core and the membrane to produce a reservoir, and connecting together the reservoir and the frame.

Mechanical Testing of Frames

The mechanical properties of the intrauterine systems, and especially of the frame, must ensure optimal uterine compatibility and user acceptability. If the mechanical strength is too low, the system could either be expulsed from the uterus or be prone to rupture. If the mechanical strength is too high, the inflexibility of the device could cause irritation or ulceration of the uterine tissue. Therefore the mechanical characteristics, flexibility and memory of the frames were assessed by using standard methods of compressing described in the literature. Flexibility is tested for characterising the property of a frame to resist low and moderate short term deformation. Memory is measured for characterising the ability of a frame to recover its shape after acute compaction.

The invention is further illustrated by the following examples.

The following abbreviations are used:

DE C2201: Desmophen® C 2201; Polycarbonate diol based on 1,6-hexanediol with a number average molecular weight Mn of 2000 g/mol; product of Bayer MaterialScience AG HDI: 1,6 Hexamethylen diisocyanate HQEE: 1,4-Di(2-hydroxyethyl)hydroquinone DDO: 1,12-Dodecanediol Cap-HDO: Chain extender based on 1,6-Hexanediol and ε-Caprolactone prepared as described in EP 1 854 818 A1, page 6, line 5.

Licowax® E: Mould release agent from Clariant GmbH

Irganox® 1010: Antioxidant from Ciba Speciality Chemicals Inc.

Irganox® MD 1024: Metal deactivator and primary (phenolic) antioxidant from Ciba Speciality Chemicals Inc.

K-KAT® 348: Bismut catalyst from King Industries Inc.

$BaSO_4$: Bariumsulfate

Description of the Production of the Thermoplastic Polyurethanes (TPUs)

Example 1

A mixture of 722.3 g DE C2201, 222.0 g HQEE, 174 g Cap-HDO, 4.5 g Irganox 1010 and 0.7 g K-Kat 348 was heated to 110° C., while stirring with a blade agitator at a speed of 500 revolutions per minute (rpm). Following this, 376.4 g HDI was added. The mixture was then stirred until the maximum possible increase in viscosity was obtained, and the TPU was then poured off. The material was thermally post-treated for 30 minutes at 80° C. and then, after cooling to room temperature, granulated. This material was used as base material for example 3.

Example 2

A mixture of 954.6 g DE C2201, 249.8 g DDO, 4.5 g Irganox 1010 and 1.0 g K-Kat 348 was heated to 125° C., while stirring with a blade agitator at a speed of 500 revolutions per minute (rpm). Following this, 290.1 g HDI was added. The mixture was then stirred until the maximum possible increase in viscosity was obtained, and the TPU was then poured off. The material was thermally post-treated for 30 minutes at 80° C. and then, after cooling to room temperature, granulated.

Example 3

385 g $BaSO_4$, 5.25 g Licowax E and 5.25 g Irganox MD 1024 were added to 1355 TPU granules prepared according example 1. The mixture was extruded on an extruder of type DSE 25/4Z, 360 Nm, having the following structure:

1. cold intake zone with conveyor elements
2. first heating zone (210° C.) with first kneading zone
3. second heating zone (225° C.) with conveyor elements and second kneading zone
4. third heating zone (225° C.) with kneading zone, conveyor elements and vacuum degassing
5. deflection head (220° C.) and die (220° C.), with a delivery rate of 4.8 kg/h and a speed of 30-40 rpm.

The extrudates were then processed to granules by means of an extrudate granulator and to injection-molded sheets by means of an injection-molding machine.

The mechanical properties of the thermoplastic polyurethane (TPU) materials of the examples 2 and 3 are presented in Table 1.

TABLE 1

| TPU material | Example 2 | Example 3 |
|---|---|---|
| MVR (5 min/10 kg/200° C.) [ml/10 min] | 13.5 | 50 |
| Shore D | 43 | 46 |
| Elongation at break [%] | 580 | 524 |
| Tensile strength [N/mm$^2$] | 34 | 27 |
| Tensile 10% [N/mm$^2$] | 5.4 | 6.4 |
| Tensile 20% [N/mm$^2$] | 7.5 | 8.7 |
| Tensile 50% [N/mm$^2$] | 10.2 | 11.2 |
| Tensile 100% [N/mm$^2$] | 12.6 | 12.6 |
| Tensile 300% [N/mm$^2$] | 18.8 | 17.1 |
| Rebound [%] | 51 | 40 |
| Flexural E-modulus [N/mm$^2$] | 88 | 100 |

Example 4

Core Preparation 98.8 parts by weight of poly(dimethylsiloxane-co-vinylmethylsiloxane) and 1.2 parts by weight of dichlorobenzoylperoxide-polydimethylsiloxane paste (50% of dichlorobenzoylperoxide) are mixed with a 2-roll mill. The mixture is extruded to form a rod with an outer diameter of 1.8 mm and cured by heat at +150° C. for 15 minutes, during which crosslinking takes place. The crosslinked core is cut into 23 mm length.

Membrane Preparation 100 parts by weight of silica-filled poly(trifluoropropylmethylsiloxane-covinylmethylsiloxane), in which the content of trifluoropropyl-methylsiloxane units was 99 mol-%; i.e. degree of trifluoropropyl substitution is 49.5%, and 1.2 parts by weight of dichlorobenzoylperoxide-polydimethylsiloxane paste (50% of dichlorobenzoylperoxide) are mixed with a 2-roll mill. The mixture is extruded into a tube-like form with a wall thickness of 0.22 mm and cured by heat.

Preparation of the Reservoir

The membrane tube of 25 mm is swelled with cyclohexane and pulled over the core. Cyclohexane is allowed to evaporate. The ends of the reservoir are closed with a silicone adhesive.

Example 5

Core Preparation

The core having the length of 18 mm is prepared according to Example 4

Membrane Preparation 99 parts of silica-filled poly(dimethylsiloxane-co-vinylmethylsiloxane), 10 ppm Pt-catalyst (of the reactant) and 0.03 parts of inhibitor (ethynyl cyclohexanol) and approximately 0.6 parts of poly(hydrogenmethylsiloxane-co-dimethylsiloxane) crosslinker are mixed in a 2-roll mill. The membrane material is extruded to a tube-like form with a wall thickness of 0.3 mm and cured by heat.

Example 6

Core Preparation 99.6 parts of commercial poly(dimethylsiloxane-co-vinylmethylsiloxane), 0.4 parts of poly(hydrogenmethylsiloxane-co-dimethylsiloxane) crosslinker, 0.02 parts of ethynyl cyclohexanol inhibitor and 10 ppm of Pt-catalyst (of the reactant) in vinyl-methyl-siloxane are mixed in a kneating mill. The mixture is extruded to a tube-like form with a wall thickness of 0.7 mm and an outer diameter of 2.6 mm. The extrudate is cured by heat at +115° C. for 30 minutes, cooled and cut to the length of 30 mm.

Membrane Preparation 9 parts of α,ω-divinylether terminated poly(ethylene oxide)-b-poly(dimethylsiloxane) multiblock copolymer (PEO-b-PDMS), 89 parts of silica-filled poly(dimethylsiloxane-covinylmethylsiloxane), 10 ppm Pt-catalyst (of the reactant), 0.03 parts inhibitor (ethynyl cyclohexanol), and approximately 2 parts of poly(hydrogenmethylsiloxane-codimethylsiloxane) crosslinker are mixed in a two-roll mill. The mixture is extruded to a tube-like form with a wall thickness of 0.15 mm and cured by heat.

Preparation of the Intrauterine System

The membrane tube having the length of 3.1 mm is swollen in isopropanol and pulled over the core. Isopropanol is allowed to evaporate. Thereafter the reservoir is swollen in isopropanol and pulled over the elongated extension of the frame comprising thermoplastic polyurethane elastomer prepared according to any one of examples 1 to 3. Isopropanol is again allowed to evaporate.

Example 7

Core Preparation 48.5 parts of PEO-b-PDMS, 49 parts of poly(dimethylsiloxane-covinylmethylsiloxane), 10 ppm Pt-catalyst (of the reactant), 0.02 parts inhibitor (ethynyl cyclohexanol), and approximately 2.4 parts of poly(hydrogenmethylsiloxane-co-dimethylsiloxane) crosslinker are mixed in a two-roll mill. The mixture is extruded to form a rod with an outer diameter of 2.1 mm and cured by heat at +150° C. for 15 minutes, during which crosslinking takes place. The crosslinked core is cut into the length of 15 mm.

The second core is prepared according to Example 6. The crosslinked core having an outer diameter of 2.1 mm is cut into the length of 10 mm.

Preparation of the Membrane and the Reservoir 9 parts of PEO-b-PDMS, 89 parts of silica-filled poly(dimethylsiloxane-co-vinylmethylsiloxane), 10 ppm Pt-catalyst (of the reactant), 0.03 parts inhibitor (ethynyl cyclohexanol), and approximately 2 parts of poly(hydrogenmethylsiloxane-co-dimethyl-siloxane) crosslinker are mixed in a two-roll mill. The membrane material is coating extruded on the above prepared two cores by successively inserting them through the inner nozzle. The formed wall thickness of the membrane is 0.2 mm.

Preparation of the Intrauterine System

The thread is first looped around the triangular frame comprising thermoplastic polyurethane elastomer prepared according to any one of examples 1 to 3. The ends of the thread are then passed through the hole in the bottom of a silver cup. Next the reservoir is placed inside the frame at the bottom apex. The bottom apex of the frame with the reservoir is pushed into the silver cup and the threads pulled tight to ensure that three parts are located and a knot tied to secure the assembly. The threads are then trimmed to the appropriate length.

Example 8

Core Preparation 48.5 parts of PEO-b-PDMS, 49 parts of poly(dimethylsiloxane-covinylmethylsiloxane), 10 ppm Pt-catalyst (of the reactant), 0.02 parts inhibitor (ethynyl cyclohexanol), and approximately 2.4 parts of poly(hydrogenmethylsiloxane-co-dimethylsiloxane) crosslinker are mixed in a two-roll mill. The mixture is extruded to form a flat, rectangular rod with slightly rounded corners and cured by heat at +150° C. for 15 minutes, during which crosslinking takes place. The outer diameters of the core are 0.9 mm (height) and 2.1 mm (width). The crosslinked core is cut into the length of 22 mm.

Preparation of the Intrauterine System

To prepare the reservoir, the core is dip-coated by a PDMS membrane having a wall thickness of 0.22 mm. A pentagonal frame with rounded corners is prepared of thermoplastic polyurethane by injection molding. The reservoir is connected to the upper part of the frame by using a modified electrical connector. The top of the clip or connector loops over the frame and is tightened around the frame. The other end, the tab, is trapped behind the reservoir which is held in place by the jaws of the connector wound around the reservoir.

Example 9

Core Preparation 54 parts of commercial poly(dimethylsiloxane-co-vinylmethylsiloxane), 45.5 parts by weight of levonorgestrel, 0.4 parts of poly(hydrogenmethylsiloxane-co-dimethylsiloxane) crosslinker, 0.02 parts of ethynyl cyclohexanol inhibitor and 10 ppm of Pt-catalyst (of the reaction species) in vinyl-methyl-siloxane were mixed in a kneating mill. The mixture was extruded and cured by heat at +115° C. for 30 minutes and cooled. The crosslinked core having an outer diameter of 2.2 mm was cut into 20 mm length.

Membrane Preparation 27 parts of α,ω-divinylether terminated poly(ethylene oxide)-b-poly(dimethylsiloxane) multiblock copolymer (PEO-b-PDMS), 71 parts of silica-filled poly(dimethylsiloxane-covinylmethylsiloxane), 10 ppm Pt-catalyst (of the reaction species), 0.03 parts inhibitor (ethynyl cyclohexanol), and approximately 2 parts of poly(hydrogenmethylsiloxane-codimethylsiloxane) crosslinker were mixed in a two-roll mill. The mixture was extruded to a tube-like form with a wall thickness of 0.22 mm and cured by heat.

Preparation of the Delivery System

The membrane was swollen in isopropanol and pulled over the core. The reservoir so formed was attached into a metal clip fixed tightly at the lower part of the pentagonal frame comprising thermoplastic polyurethane elastomer.

Example 10

Preparation of the Intrauterine System Comprising the Frame, the Reservoir, a Silver Ring and the Removal Thread The frame is injection moulded. Molten thermoplastic is injected at high pressure into a mould, which is the inverse of the frame shape. The moulded frame is ejected from the tool and when it is cooled down the gate and spigot are removed and any flash is trimmed off. Next the silver ring and the prefabricated tube-like reservoir are assembled onto the central shaft of the frame. The free end of the central shaft is then heat formed to create a physical retention feature to mechanically retain the reservoir and prevent it from sliding off. Next the thread is looped through the frame and secured with a knot. The threads are then trimmed to the appropriate length.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. An intra-uterine system for a long-term insertion into a uterine cavity comprising:
   a rectangular reservoir; and
   a continuous, closed and flexible frame of a polygonal shape,
   wherein a first end of the reservoir is connected to an inner surface of the frame, the reservoir comprises at least one therapeutically active substance and the frame comprises a thermoplastic polyurethane elastomer comprising the reaction product of:
   a) an isocyanate component comprising:
      a1) from 80 to 100 mol. % of 1,6-hexamethylene diisocyanate
   b) a polyol component comprising a polycarbonate diol that is prepared from 1,6-hexanediol and dimethyl carbonate,
   c) a chain extender component comprising:
      c1) from 35 to 95 mol. % of at least one difunctional chain extender selected from 1,2-ethanediol, 1,3-propanediol, 1,4-butanediol, 1,6-hexanediol, 1,8-octanediol, 1,10-decanediol, 1,12-dodecanediol or hydroquinone bis-2-hydroxyethyl ether (HQEE) and mixtures of a straight chain oligomer, prepared from 1,6-hexanediol and ε-caprolactone, and hydroquinone bis-2-hydroxyethyl ether (HQEE), and
      c2) from 5 to 65 mol. % of a chain extender selected from 1,2-ethanediol, 1,3-propanediol, 1,4-butanediol, 1,6-hexanediol, 1,8-octanediol, 1,10-decanediol, 1,12-dodecanediol or hydroquinone bis-2-hydroxyethyl ether (HQEE) and mixtures of a straight chain oligomer, prepared from 1,6-hexanediol and ε-caprolactone, and hydroquinone bis-2-hydroxyethyl ether (HQEE) which is different from the difunctional chain extender of c1
   in the presence of
   d) one or more catalysts selected from, bismuth neodecanoate, bismuthoctoate, bismuth carboxylate (BiCat), stannous diacetate, stannous dioctoate, stannous dilaurate, or dibutyltin diacetate, dibutyltin dilaurate, dibutyltin dioctoate, titanic esters or ferric acetylacetonate,
   with the addition of
   e from 0.1 to 35 wt. %, based on the weight of the thermoplastic polyurethane made of components a) to d), of inorganic fillers, and
   f further additives or auxiliary substances in which the ratio of the isocyanate groups of a) to isocyanate-reactive groups of b), and c) is from 0.9:1 to 1.1:1;
   wherein the thermoplastic polyurethane elastomer has at least one of a degree of stiffness that is greater than 8 N/mm2 at 100% elongation, a high hardness of Shore D>40 and <55, and a rebound of greater than 30%.

2. An intrauterine system according to claim 1, characterized in that the chain extender component is a mixture of hydroquinone bis(2-hydroxyethyl)ether and a straight chain oligomer prepared from 1,6-hexanediol and -caprolactone.

3. An intrauterine system according to claim 1, characterized in that the chain extender component is 1, 12-dodecane diol.

4. An intrauterine system according claim 1, characterized in that the frame is essentially triangular or pentagonal.

5. An intra-uterine system according to claim 1, characterized in that the cross section of the frame is circular, semi-circular, oval, flat, elliptical, rectangular, angular, polygonal or star-shaped.

6. An intra-uterine system according to claim 1, characterized in that both the first end and a second end end-of the reservoir are connected to the inner surf ace of the frame.

7. An intra-uterine system according to claim 1, characterized in that the cross section of the reservoir is circular, oval, flat, elliptical, rectangular, angular, polygonal or star-shaped.

8. An intra-uterine system according to claim 1, characterized in that the reservoir comprises at least one core.

9. An intra-uterine system according to claim 8, characterized in that at least one of the cores of the reservoir is encased by a polymer layer.

10. An intra-uterine system according to claim 9, characterized in that the polymer layer includes a polymer composition and the polymer composition of said at least one core and the polymer layer encasing the core are the same or different.

11. An intra-uterine system according to claim 1, characterized in that the frame comprises a supporting means consisting of a polymer composition or a biocompatible metal.

* * * * *